Figure 1:
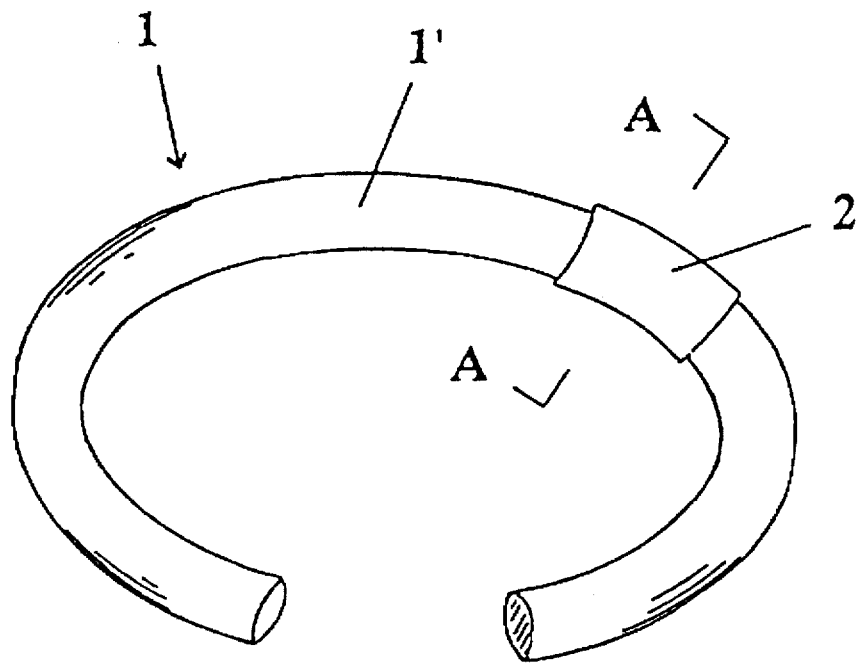

United States Patent [19]
Lehtinen et al.

[11] Patent Number: 5,694,947
[45] Date of Patent: Dec. 9, 1997

[54] INTRAVAGINAL DELIVERY SYSTEM

[75] Inventors: Matti Lehtinen, Piispanristi; Christine Talling, Turku, both of Finland

[73] Assignee: Leiras Oy, Turku, Finland

[21] Appl. No.: 564,253

[22] PCT Filed: Jun. 15, 1994

[86] PCT No.: PCT/FI94/00255

§ 371 Date: Apr. 11, 1996

§ 102(e) Date: Apr. 11, 1996

[87] PCT Pub. No.: WO95/00199

PCT Pub. Date: Jan. 5, 1995

[30] Foreign Application Priority Data

Jun. 17, 1993 [FI] Finland .................... 932789

[51] Int. Cl.[6] ........................ A61F 6/06
[52] U.S. Cl. ................... 128/833; 128/832
[58] Field of Search ................... 128/830–841

[56] References Cited

U.S. PATENT DOCUMENTS

| | | |
|---|---|---|
| 3,920,805 | 11/1975 | Roseman . |
| 3,967,618 | 7/1976 | Zaffaroni ............. 128/833 |
| 3,973,560 | 8/1976 | Emmett ............. 128/833 |
| 4,012,496 | 3/1977 | Schöpflin et al. . |
| 4,292,965 | 10/1981 | Nash et al. . |
| 4,596,576 | 6/1986 | de Nijs . |

FOREIGN PATENT DOCUMENTS

| | | |
|---|---|---|
| 0 050 867 A1 | 5/1982 | European Pat. Off. . |
| 0 082 894 A1 | 7/1983 | European Pat. Off. . |
| 661 874 A5 | 8/1987 | Switzerland . |

*Primary Examiner*—Michael A. Brown

[57] ABSTRACT

Intravaginal delivery system including a flexible support means, and a delivery means carried by the support means and containing an active agent wherein the support means comprises a core member substantially in the form of an open ring, and the delivery means comprises at least one polymer body which encircles the core member in a beltwise manner along a portion of a length of the core member.

12 Claims, 1 Drawing Sheet

INTRAVAGINAL DELIVERY SYSTEM

The object of the present invention is an intravaginal delivery system, which comprises a flexible support means and a delivery means containing active agent and carried by the support means. Such delivery systems are used for administering various active and therapeutical agents which are absorbed through the vagina, for example for the administration of hormones in menopausal treatment.

A number of different constructional solutions of drug and contraceptive rings is known from literature. The simplest solutions are such wherein the delivery system is simply formed by a drug-containing polymer matrix in the form of a closed ring (U.S. Pat. No. 3,545,439). A variety of this is a closed ring which comprises a drug-free core surrounded by a drug matrix optionally containing a number of different drugs and in addition optionally an outermost polymer membrane (U.S. Pat. No. 3,920,805, U.S. Pat. No. 4,292,965). These solutions have the common disadvantage that the release of drug from these is difficult to regulate, which problem is enhanced in connection with a drug mixture.

A solution different from the above mentioned is disclosed for example in the U.S. Pat. No. 4,012,496, wherein the drug containing part of the ring is formed by one or several drug matrix strings embedded in a groove extending along the periphery of the ring and each containing only one drug. Depending on the particular drug and its release characteristics, the drug string can in some instances be very thin, which in turn gives rise to production-technical problems. An additional disadvantage in this construction is that the active agent has a tendency to diffuse from the drug string into the polymer body, which for its own part makes it difficult to control the release of the drug.

The simultaneous administration of several drugs by means of an intravaginal ring has been disclosed also in the U.S. Pat. No. 4,596,576. In this patent a solution is disclosed wherein active agent containing containers are mounted along the periphery of the ring, which containers are separated from each other with a plug or similar made from an inert material, which prevents the migration of drug from one container to the other, in order to ensure disturbance-free release of the drugs in the desired proportion. Metals, such as noble metals, glass, ceramics etc. have been suggested for use a inert materials. Also this solution is difficult from a production-technical viewpoint as different sized tube-shaped bodies of different materials are used, which have to be connected by gluing or in some other way.

The object of the present invention is to eliminate the disadvantages relating to the above mentioned known solutions, by providing a solution which is easy to manufacture and which guarantees the release of the drug or drugs in a controlled manner and in the correct proportions. The solution according to the invention is characterized in that the support means consists of a core member substantially in the form of an open ring, and the delivery means consists of at least one sleeve-like polymer body which encircles the core member in a beltwise manner along a part of the length of the core member.

The support means is naturally made of a material which is biologically compatible and remains unchanged also for prolonged periods of time in the conditions prevailing in the vagina.

According to the invention, the inner surface of the sleeve-like body is preferably in contact with a material, which substantially prevents the migration of active agent into the support means. Accordingly, part of the support means, such as its outer surface, at least adjacent the (sleeve-like body), or the support means in its entirety, can be made from a material which is substantially inert with respect to the active agent in the sleeve-like body. The term "substantially inert" means in this connection that the said active agent cannot, to any substantial degree, diffuse or in any other way migrate from the sleeve-like body into the support means. Suitable support or carrier materials are the following flexible polymer materials: cross-linked rubbers, such as e.g. natural rubber, butyl rubber and polydimethylsiloxane elastomers, flexible thermoplastic resins, such as ethylvinylacetate (EVA), thermoplastic elastomers, such as styrene copolymers (SEBS, SBS, SIS), polyurethanes and thermoplastic polyolefins.

The support means can be prepared in a simple manner from a suitable polymeric material, for example by compressing, such as in a mould, or extruding to form (rod-like member) with a suitable diameter, and by cutting from the extrudate pieces of suitable length to form the core member, which is vulcanized into the desired, substantially annular shape. The core member can be of solid polymer or hollow. In its simplest embodiment, the cross-section of the core member is substantially circular, whereby the cross-section refers to the cross-section in a plane containing the axis of the open ring formed by the core member.

In the delivery system according to the invention, the actual delivery means is formed by one or several sleeve- or shell-shaped bodies mounted, e.g. threaded onto the core member, and beltwise encircling or enveloping the same, which sleeve-like bodies contain polymer and active agent. Advantageously the cross-section of the sleeve-like body substantially corresponds to the cross-section of the core member. The sleeve-like body extends along part of the length of the core member, whereby the degree of extension can vary, and depends on a number of factors, such as choice of materials and choice of active agents etc. Thus the length of a sleeve is shorter, typically only a fraction of the length of the core member. If several sleeves are used, such sleeves typically also extend only over a part of the length of the core member. The thickness and shape of the sleeve wall depends on materials and active agents used as well as desired release profiles, but generally the thickness is only a fraction of the thickness of the core member.

If there are several sleeve-like bodies the different bodies may advantageously contain different active agents, in order to allow for a combination treatment. According to the invention, the sleeve-like bodies can, however, also contain the same active agent. This solution is advantageous from a production-technical view point when the amount of drug to be administered is large, whereby a single sleeve can be made smaller and thus easier to mount onto the support means.

Polymers suitable for the purpose are such wherein the active agents can diffuse from the sleeve into the vagina. Suitable materials are, for example, organic polysiloxanes, such as polydimethylsiloxane, polyurethane, EVA-copolymers. As the basic release rate level of the active agent is dependant of the surface area of the sleeve-like body, the release rate may be changed also by changing the surface area.

The choice of polymer used both in the support means and the sleeve depends also on the selected active agent. Thus, for example, for some active agents a sleeve made from EVA-polymer can be used on a support ring of SEBS, whereas for other polymers an EVA-support ring in combination, for example, with a siloxane sleeve is suitable.

According to an advantageous embodiment of the invention, the rate of release of active agent can be regulated also by means of a membrane coating surrounding the sleeve-like body, for example a polysiloxane membrane, whereby the release rate is regulated also by adjusting the thickness of the membrane.

According to an embodiment of the invention, the inner surface of the sleeve-like body can be coated with an inert, diffusion-preventing material, such as a suitable polymer film. According to an alternative solution, such an inert layer may form an independent protective layer between the inner surface of the sleeve and the outer surface of the support means.

The sleeve-like body may be manufactured in a simple manner by compressing, e.g. in a mould, or by extruding a mixture containing active agent and polymer and cutting the extrudate into pieces of suitable length. In case the sleeve-like body is coated with a membrane or provided on its inner surface with an inert layer, the sleeve-like body is advantageously prepared using coextrusion of the active agent matrix, membrane and/or inner surface or by coating in some other manner. The sleeve-like body can also be prepared by first preparing a sheet-like body, optionally coated with a membrane polymer, from which strips of a suitable size are cut and rolled to form a sleeve, the seam of which is closed with glue or by welding.

The sleeve-like body is mounted on the support means preferably by first enlarging its diameter to some degree and thereafter by simply sliding it into the support means. When the sleeve-like body is of a silicone resin or a cross-linked rubber, the enlargement can take place, for example, by swelling the sleeve-like body in a suitable organic solvent, whereafter the swollen body is mounted onto the support means and the solvent is evaporated, whereby the sleeve tightens onto the support means.

As an alternative, the sleeve-like body can be stretched mechanically with a suitable device and threaded in the stretched state onto the support means. When the stretching force is discontinued, the sleeve-like body is tightened onto the support means.

By means of the delivery system, any active agent can be administered which is suitable for intravaginal use. Thus, for example, various drugs for the treatment of infections of viral, fungal or bacterial origin, or different types of hormones, for example, for the treatment menopause problems, can come into question. Especially it is possible, by means of the system of the invention, to carry out a combination treatment with estrogenic and progestational hormones.

By means of the delivery system according to the invention it is possible to obtain almost linear release of active agent with respect to the surface area of the sleeve, without the uncontrolled release of active agent in the initial stages of use (so-called burst effect which is due to the diffusion of active agent into the support ring). The release profile can be further regulated, as described above, by means of a membrane, especially by regulating its thickness.

Tests carried out have shown in addition that no differences between the retention of an open ring and a closed ring during use could be observed. In fact it has been observed that the additional flexibility brought about by the open form of the ring makes the ring easier to insert. It can also be manufactured and used in one size suitable for all women, which is a production technical advantage.

Figure 2:
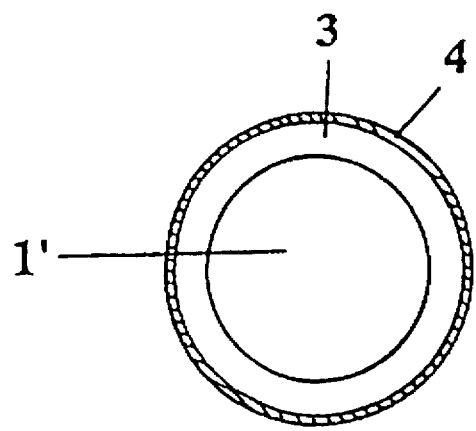
Figure 3:
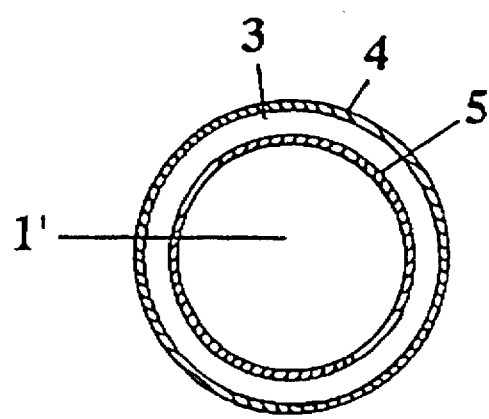

In the following the invention is illustrated in more detail by referring to the enclosed drawing, wherein FIG. 1 shows, in perspective, an embodiment of the system according to the invention, FIG. 2 shows a cross-section along the line A—A of FIG. 1, and FIG. 3 shows a cross-section of an alternative ambodiment.

In the drawing an embodiment of a delivery system according to the invention is disclosed, which is intended for the administration of a single active agent. It is comprised by a support means 1 in the form of an open ring-shaped core member 1'. The cross-section of the core member is substantially circular. It is made from a polymeric material which is at least to some degree flexible. Onto the support means, a sleeve-like body 2 has been mounted, which forms the actual delivery means of the active agent. The construction of this sleeve-like body is better apparent from FIG. 2, which shows a cross-section through the core member. The delivery means comprises in the embodiment shown an active agent containing polymer matrix 3, and a membrane coating 4. In the embodiment shown in the FIGS. 1 and 2 the material in the support means 1 is substantially inert with respect to the active agent, or its outermost layer is of such a material so that the active agent cannot migrate into the support means itself and thus disturb the release profile. It is also apparent that the inner diameter of the sleeve 2 is substantially equal to the outer diameter of the core member.

In the FIG. 3 an alternative construction of the sleeve-like body is shown, which can be used with support means made from polymers different from the afore mentioned inert polymers. In this embodiment, in addition to the layers shown in FIG. 2, there is an inner layer 5 preventing the diffusion of the active agent.

In case two or more active agents are to be administered simultaneously, a corresponding number of sleeves threaded onto the same support means is used.

In the following the results from release tests are shown wherein on the one hand the release of a progestational and on the other hand of an estrogenic agent have been tested. In the test system a glass rod was used to simulate the support means. Onto the glass rod a sleeve-like matrix body made from a tape and containing one each of the active agents and polydimethylsiloxane, was threaded. In addition, the sleeve-like body was in some tests coated with a polydimethylsiloxane membrane. The amount of released drug was measured in a shaking device in a 0.9% NaCl-solution at 37° C. The following results were obtained:

Test 1:
Matrix: levonorgestrel: polydimethylsiloxane (1:9)
Membrane: polydimethylsiloxane

| Surface-area of matrix tape (cm²) | Membrane thickness (mm) | In vitro release (µg/day) |
| --- | --- | --- |
| 2.8 | 0 | 60 |
| 2.8 | 0.5 | 25 |
| 5.6 | 0 | 100 |
| 5.6 | 0.5 | 60 |

Test 2:
Matrix: 17-beta-estradiol: polydimethylsiloxane (1:9)
Membrane: polydimethylsiloxane

| Surface-area of matrix tape (cm²) | Membrane thickness (mm) | In vitro release (µg/day) |
| --- | --- | --- |
| 1.4 | 0 | 80 |
| 1.4 | 0.5 | 8 |
| 2.8 | 0.5 | 14 |
| 5.6 | 0.5 | 27 |

From the results it can be seen that the release of each drug is almost linear to the surface area of the matrix sleeve. This is true both for the membrane coated and uncoated sleeve.

The delivery system has been compared also to its ease of use to an ordinary closed ring. The test persons were 12 voluntary women, age over 18. The test persons used each ring consecutively for five days. After a ring period, a ring-free period of two days followed.

The outer diameters of the rings according to the invention were 50 and 54 mm, respectively and that of the closed ring 54 mm. All rings were of polydimethylsiloxane. In the test, properties such as appearance, size, shape, application, handling, feel, pain, movability etc. were tested.

According to the results, the open ring was at least as good as the closed ring, which has been clinically extensively studied. As to some characteristics, the smaller ring was better tolerated than the larger.

We claim:

1. Intravaginal delivery system comprising a flexible support means, and a delivery means carried by the support means and containing an active agent wherein the support means comprises a core member substantially in the form of an open ring, and the delivery means comprises at least one polymer body which encircles the core member in a beltwise manner along a portion of a length of the core member.

2. The delivery system according to claim 1 wherein the polymer body comprises a substance which is selected from the group consisting of polysiloxane, polyurethane and EVA-copolymer.

3. The delivery system according to claim 1 wherein the support means comprises a material selected from the group consisting of a crosslinked rubber, a flexible thermoplastic resin, a thermoplastic elastomer, a polyurethane and a thermoplastic polyolefin.

4. The delivery system according to claim 1 wherein the polymer body has an inner surface which is in contact with a material which substantially prevents the migration of the active agent from the polymer body into the support means.

5. The delivery system of claim 4 wherein the support means consists essentially of a material preventing the migration of active agent.

6. The delivery system according to claim 1 wherein the delivery means is formed by two sleeve-like bodies each containing a different active agent.

7. The delivery system according to claim 1 wherein the polymer body contains a progestational agent or an estrogenic agent.

8. The delivery system according to claim 1 wherein the delivery system comprises two sleeve-like bodies, both containing the same active agent.

9. The delivery system according to claim 1 wherein the polymer body is coated with a membrane allowing diffusion of the active agent.

10. Method for preparing a delivery system according to claim 1, wherein the diameter of the polymer body containing the active agent and the polymer is enlarged mechanically or by swelling, and is mounted in this condition onto the core member, and is allowed to tighten onto the support means.

11. The method according to claim 10 wherein the polymer body is made by coextrusion together with a polymeric membrane which forms an outer layer on the sleeve when mounted on the core member.

12. Method of treating menopause in a human female comprising implanting in the vagina of the female a device for delivering a selected drug for treating menopause, the device comprising a flexible support mechanism and a delivery mechanism carried by the support mechanism, the delivery mechanism containing a selected drug, wherein the support mechanism comprises a core member substantially in the form of an open ring and wherein the delivery mechanism comprises at least one polymer body which encircles the core member in a beltwise manner along a portion of a length of the core member.

* * * * *